(12) United States Patent
Brown

(10) Patent No.: US 10,624,666 B2
(45) Date of Patent: Apr. 21, 2020

(54) ULTRASONIC TRANSMISSION COMPONENTS OF ULTRASONIC SURGICAL INSTRUMENTS AND METHODS OF MANUFACTURING THE SAME

(71) Applicant: COVIDIEN LP, Mansfield, MA (US)

(72) Inventor: Michael J. Brown, Superior, CO (US)

(73) Assignee: Covidien LP, Mansfield, MA (US)

( * ) Notice: Subject to any disclaimer, the term of this patent is extended or adjusted under 35 U.S.C. 154(b) by 257 days.

(21) Appl. No.: 15/666,656

(22) Filed: Aug. 2, 2017

(65) Prior Publication Data
US 2019/0038307 A1   Feb. 7, 2019

(51) Int. Cl.
| | | |
|---|---|---|
| A61B 17/32 | (2006.01) | |
| A61B 17/22 | (2006.01) | |
| B33Y 10/00 | (2015.01) | |
| B33Y 80/00 | (2015.01) | |
| A61B 17/00 | (2006.01) | |
| A61B 18/00 | (2006.01) | |
| A61B 17/29 | (2006.01) | |

(52) U.S. Cl.
CPC .. *A61B 17/320068* (2013.01); *A61B 17/2202* (2013.01); *A61B 17/22012* (2013.01); *A61B 17/320092* (2013.01); *B33Y 10/00* (2014.12); *B33Y 80/00* (2014.12); *A61B 2017/00349* (2013.01); *A61B 2017/00526* (2013.01); *A61B 2017/00734* (2013.01); *A61B 2017/22014* (2013.01); *A61B 2017/2945* (2013.01); *A61B 2017/320069* (2017.08); *A61B 2017/320073* (2017.08); *A61B 2017/320074* (2017.08); *A61B 2017/320094* (2017.08); *A61B 2018/00023* (2013.01)

(58) Field of Classification Search
CPC .................. B33Y 10/00; A61B 17/320068
USPC ........................................................ 419/5
See application file for complete search history.

(56) References Cited

U.S. PATENT DOCUMENTS

| | | |
|---|---|---|
| 5,383,876 A | 1/1995 | Nardella |
| 5,391,144 A | 2/1995 | Sakurai et al. |

(Continued)

FOREIGN PATENT DOCUMENTS

| | | |
|---|---|---|
| CN | 201939898 U | 8/2011 |
| EP | 00514810 A1 | 11/1992 |

(Continued)

OTHER PUBLICATIONS

Extended European Search Report issued in corresponding EP Application No. 18186751.6 dated Dec. 21, 2018, 6 pages.

(Continued)

*Primary Examiner* — Weiping Zhu

(57) ABSTRACT

A method of manufacturing an ultrasonic transmission component of an ultrasonic surgical instrument includes forming, via additive manufacturing, a waveguide, including a body portion, a curved blade extending distally from the body portion, and a lumen extending through a portion of the body portion and a portion of the curved blade. Another method of manufacturing an ultrasonic transmission component of an ultrasonic surgical instrument includes forming, via additive manufacturing, a waveguide, including a body portion and a blade extending distally from the body portion. At least one of the body portion or the blade defines a varied density.

17 Claims, 3 Drawing Sheets

(56) References Cited

U.S. PATENT DOCUMENTS

| | | | |
|---|---|---|---|
| 6,142,992 | A | 11/2000 | Cheng et al. |
| 6,206,876 | B1 | 3/2001 | Levine et al. |
| 6,379,371 | B1 | 4/2002 | Novak et al. |
| 6,633,234 | B2 | 10/2003 | Wiener et al. |
| 6,764,487 | B2 | 7/2004 | Mulier et al. |
| 7,074,219 | B2 | 7/2006 | Levine et al. |
| 7,404,816 | B2 | 7/2008 | Abboud et al. |
| 7,530,986 | B2 | 5/2009 | Beaupre et al. |
| 8,628,534 | B2 | 1/2014 | Jones et al. |
| 8,974,478 | B2 | 3/2015 | Ross et al. |
| 9,044,261 | B2 | 6/2015 | Houser |
| 9,113,930 | B2 | 8/2015 | Reid, Jr. |
| 9,113,943 | B2 | 8/2015 | Ross et al. |
| 2003/0181904 | A1 | 9/2003 | Levine et al. |
| 2005/0209578 | A1 | 9/2005 | Evans et al. |
| 2008/0015563 | A1 | 1/2008 | Hoey et al. |
| 2009/0287201 | A1 | 11/2009 | Lalonde et al. |
| 2011/0077635 | A1 | 3/2011 | Bonn |
| 2011/0152759 | A1* | 6/2011 | Clymer .............. A61B 10/0283 604/93.01 |
| 2014/0303611 | A1 | 10/2014 | Shadduck et al. |
| 2015/0007704 | A1 | 1/2015 | Vieira |
| 2015/0073457 | A1 | 3/2015 | Stoddard et al. |
| 2015/0073458 | A1 | 3/2015 | Stoddard et al. |
| 2015/0165240 | A1 | 6/2015 | Stoddard et al. |
| 2015/0197063 | A1* | 7/2015 | Shinar .................... G06F 17/50 700/98 |

FOREIGN PATENT DOCUMENTS

| | | |
|---|---|---|
| EP | 2572660 A2 | 3/2013 |
| WO | 2011151837 A1 | 12/2011 |

OTHER PUBLICATIONS

European Examination Report dated Jan. 31, 2020 issued in corresponding EP Appln. No. 18 186 751.6.

* cited by examiner

US 10,624,666 B2

ULTRASONIC TRANSMISSION COMPONENTS OF ULTRASONIC SURGICAL INSTRUMENTS AND METHODS OF MANUFACTURING THE SAME

BACKGROUND

Technical Field

The present disclosure relates to ultrasonic surgical instruments and, more specifically, to ultrasonic transmission components, e.g., waveguides, end effectors, etc., of ultrasonic surgical instruments and methods of manufacturing ultrasonic transmission components of ultrasonic surgical instruments.

Background of Related Art

Energy-based tissue treatment is well known in the art. Various types of energy (e.g., electrical, ultrasonic, microwave, cryogenic, thermal, laser, etc.) are applied to tissue to achieve a desired result. Ultrasonic energy, for example, may be delivered to tissue to treat, e.g., coagulate and/or cut, tissue.

Ultrasonic surgical instruments, for example, typically include a waveguide having a transducer coupled thereto at a proximal end of the waveguide and an end effector disposed at a distal end of the waveguide. The waveguide transmits ultrasonic energy produced by the transducer to the end effector for treating tissue at the end effector. The end effector may include a blade, hook, ball, shears, etc., and/or other features such as one or more jaws for grasping or manipulating tissue.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

Provided in accordance with aspects of the present disclosure is a method of manufacturing an ultrasonic transmission component of an ultrasonic surgical instrument including forming, via additive manufacturing, a waveguide. The waveguide is formed to include a body portion and a curved blade extending distally from the body portion and to define a lumen extending through a portion or the entirety of the body portion and a portion or the entirety of the curved blade.

In aspects of the present disclosure, the waveguide is formed via Direct Metal Laser Sintering. Alternatively, the waveguide is formed via Selective Laser Sintering or other additive manufacturing technique.

In aspects of the present disclosure, the method further includes modeling the waveguide using a computer-aided design program and using the modeled waveguide to form the waveguide via additive manufacturing.

In aspects of the present disclosure, the lumen extends a majority of a length of the body portion and a majority of a length of the curved blade. The lumen may additionally or alternatively define a closed distal end portion.

In aspects of the present disclosure, the waveguide is formed from titanium.

In aspects of the present disclosure, the body portion and/or the curved blade are formed to include a varied density. Additionally or alternatively, at least a portion of the body portion and/or at least a portion of the curved blade are formed to include a lattice structure.

In aspects of the present disclosure, the method further includes inserting an inner tube at least partially into the lumen.

Another method of manufacturing an ultrasonic transmission component of an ultrasonic surgical instrument provided in accordance with aspects of the present disclosure includes forming, via additive manufacturing, a waveguide including a body portion and a blade extending distally from the body portion. The body portion and/or the blade defines a varied density.

In aspects of the present disclosure, the waveguide is formed via Direct Metal Laser Sintering. Alternatively, the waveguide is formed via Selective Laser Sintering or other additive manufacturing technique.

In aspects of the present disclosure, the method further includes modeling the waveguide using a computer-aided design program and using the modeled waveguide to form the waveguide via additive manufacturing.

In aspects of the present disclosure, the waveguide is further formed to define a lumen extending through a portion of the body portion and a portion of the blade. The lumen, in aspects, may extend a majority of a length of the body portion and/or a majority of a length of the blade. The method may further include inserting an inner tube at least partially into the lumen.

In aspects of the present disclosure, the waveguide is formed from titanium.

In aspects of the present disclosure, at least a portion of the body portion and/or at least a portion of the blade is formed to include a lattice structure.

In aspects of the present disclosure, the blade is curved.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

The present disclosure provides ultrasonic transmission components of ultrasonic surgical instruments and methods of manufacturing the same. Although detailed below with respect to ultrasonic surgical instrument 10 (FIG. 1), the aspects and features of the present disclosure are equally applicable for use with other ultrasonic surgical instruments. For the purposes herein, ultrasonic surgical instrument 10 (FIG. 1) is general described.

Figure 1:
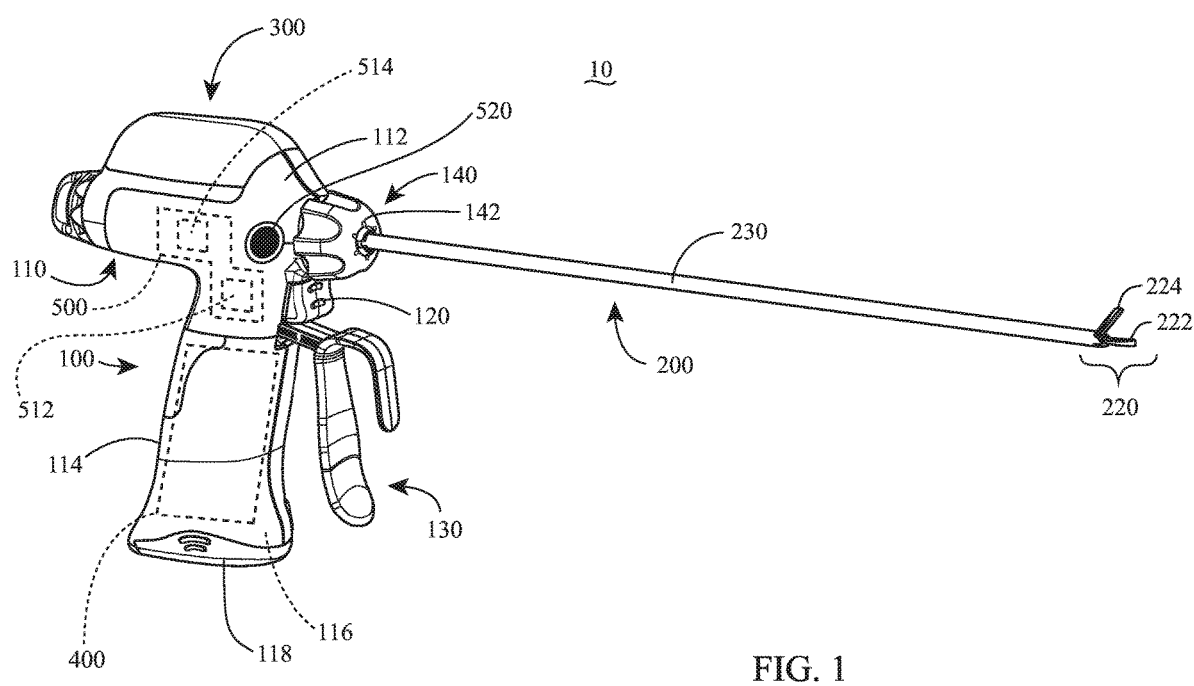
FIG. 1 is a perspective view of an ultrasonic surgical instrument provided in accordance with the present disclosure.

Referring generally to FIG. 1, an ultrasonic surgical instrument provided in accordance with the aspects and features of the present disclosure is shown generally identified by reference numeral 10. Ultrasonic surgical instrument 10 generally includes a handle assembly 100, an elongated assembly 200 extending distally from handle assembly 100, an ultrasonic transducer and generator assembly ("TAG") 300 configured for releasable engagement with handle assembly 100, a battery assembly 400 configured for releasable receipt within handle assembly 100, and a cooling system 500 operably disposed within and extending through handle assembly 100 and elongated assembly 200. Thus, ultrasonic surgical instrument 10 is configured as a cordless, hand-held device. However, the present disclosure is equally applicable for use with corded ultrasonic surgical instruments configured to connect to a remote generator.

Handle assembly 100 includes a housing 110 defining a body portion 112 configured to enable releasable mounting of TAG 300 thereon and a fixed handle portion 114 depending from body portion 112. Fixed handle portion 114 defines a battery compartment 116 including a door 118 configured to enable releasable receipt and enclosure of battery assembly 400 within fixed handle portion 114. Handle assembly 100 further includes an activation button 120 operably positioned to electrically couple between TAG 300 and battery assembly 400 when TAG 300 is mounted on body portion 112 of housing 110 and battery assembly 400 is enclosed within compartment 116 of fixed handle portion 114 of housing 110 to enable selective energization of ultrasonic surgical instrument 10, as detailed below.

A clamp trigger 130 extends from housing 110 of handle assembly 100 adjacent fixed handle portion 114 of housing 110. Clamp trigger 130 includes a drive portion (not shown) extending into body portion 112 of housing 110 and operably coupled to a drive assembly (not shown) to enable actuation of ultrasonic surgical instrument 10 in response to actuation of clamp trigger 130 relative to fixed handle portion 114 of housing 110, as also detailed below.

Figure 2:
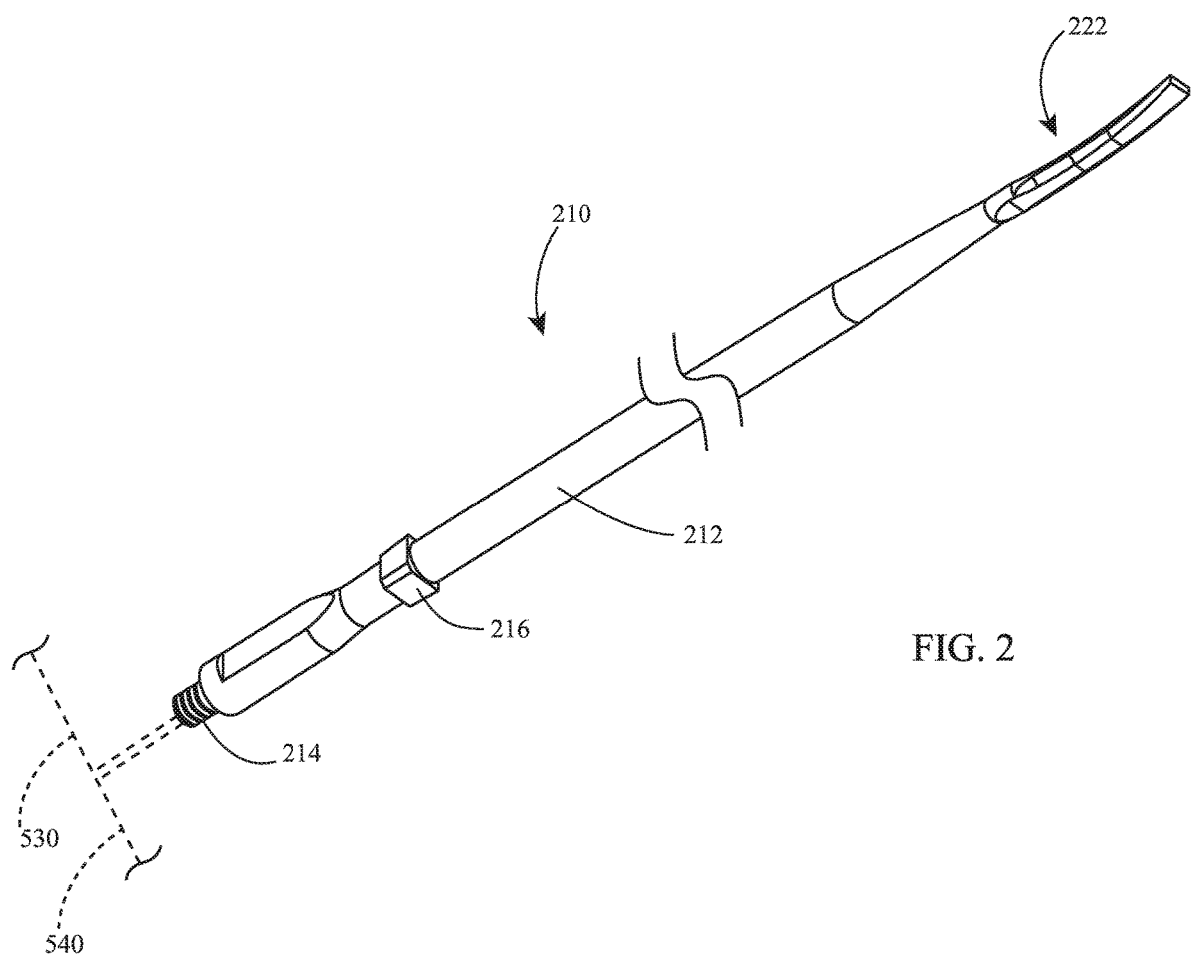
FIG. 2 is a perspective view of a waveguide of the ultrasonic surgical instrument of FIG. 1.

With additional reference to FIG. 2, elongated assembly 200 of ultrasonic surgical instrument 10 includes a waveguide 210 which extends from housing 110 to an end effector 220 disposed at the distal end portion of elongated assembly 200. Elongated assembly 200 further includes an outer tube 230 and an inner tube (not shown). Waveguide 210 includes a body portion 212 that extends through housing 110 and outer tube 230 and a distal end portion that extends distally from outer tube 230 and defines blade 222 of end effector 220. Waveguide 210 may be formed from titanium, a titanium alloy, or other suitable material(s). The proximal end portion of body portion 212 of waveguide 210 includes features, e.g., threading 214, configured to enable operable engagement thereof with TAG 300, e.g., with a female threaded receiver (not shown) of the transducer of TAG 300.

Outer tube 230 is slidably disposed about waveguide 210 and extends between housing 110 and end effector 220. A rotating assembly 240 is rotatably mounted on housing 110 and operably coupled to elongated assembly 200 so as to enable rotation of elongated assembly 200 and, thus, end effector 220 relative to housing 110 upon rotation of rotation wheel 242 of rotating assembly 240 relative to housing 110.

End effector 220 is disposed at a distal end portion of elongated assembly 200 and includes blade 222 of waveguide 210 and a jaw member 224. Jaw member 224 is pivotable relative to blade 222 between an open position, wherein jaw member 224 is spaced-apart from blade 222, and a closed position, wherein jaw member 224 is approximated relative to blade 222 in juxtaposed alignment therewith for clamping tissue therebetween. Jaw member 224 is operably coupled to the distal end portion of outer tube 230 and a proximal end portion of outer tube 230, in turn, is operably coupled to clamp trigger 130 by way of the drive assembly (not shown) such that jaw member 224 is movable between the open position and the closed position in response to actuation of clamp trigger 130 relative to fixed handle portion 114 of housing 110 of handle assembly 100.

Blade 222 is configured to serve as an active or oscillating ultrasonic member that is selectively activatable to ultrasonically treat tissue grasped between blade 222 and jaw member 224. As shown in FIG. 2, blade 222 is formed to define a curved configuration, although straight configurations are also contemplated. Blade 222 may be curved in any direction relative to jaw member 224, for example, such that the distal tip of blade 222 is curved towards jaw member 224, away from jaw member 224, or laterally (in either direction) relative to jaw member 224. Further, blade 222 may be formed to include multiple curves in similar directions, multiple curves in different directions within a single plane, and/or multiple curves in different directions in different planes. Blade 222 may additionally or alternatively be formed to include a tapered configuration, various different cross-sectional configurations along its length, cut-outs, indents, edges, protrusions, straight surfaces, curved surfaces, angled surfaces, wide edges, narrow edges, and/or other features. Blade 222 may also be formed to include a varying density and/or a lattice structure to reinforce portions thereof, provide increased flexibility in portions thereof, increase or decrease displacement of portions thereof, increase or decrease operating temperature of portions thereof, etc. Put more generally, blade 222 may be formed to include any suitable configuration and/or features to facilitate use in a particular fashion(s), achieve a particular tissue effect(s), generate particular resonant frequency(s), facilitate a particular heating and/or cooling profile, etc.

Body portion 212 of waveguide 210 may likewise be formed to include various features. As noted above, body portion 212 of waveguide 210 includes threading 214 to enable threaded engagement of waveguide 210 with TAG 300 (FIG. 1). Body portion 212 of waveguide 210 may further include a torque block 216 formed thereon towards a proximal end portion thereof to facilitate coupling of waveguide 210 with rotating assembly 240. Body portion 212 of waveguide 210 may additionally or alternatively include a tapered configuration, various different cross-sectional configurations along its length, flats, various different diameters, coupling features to facilitate coupling of waveguide 210 to other components of ultrasonic surgical instrument 10 (FIG. 1), and/or other features. Body portion 212 of waveguide 210 may also be formed to include a varying density and/or a lattice structure to reinforce portions thereof, provide increased flexibility in portions thereof, etc. Put more generally, body portion 212 of waveguide 210, like blade 222, may be formed to include any suitable configuration and/or features to facilitate use in a particular fashion(s), achieve a particular tissue effect(s), generate particular resonant frequency(s), facilitate a particular heating and/or cooling profile, etc. Body portion 212 of waveguide 210 and blade 222 may be monolithically formed, e.g., from a titanium alloy, or may be separately formed and then connected to one another.

Figure 3A:
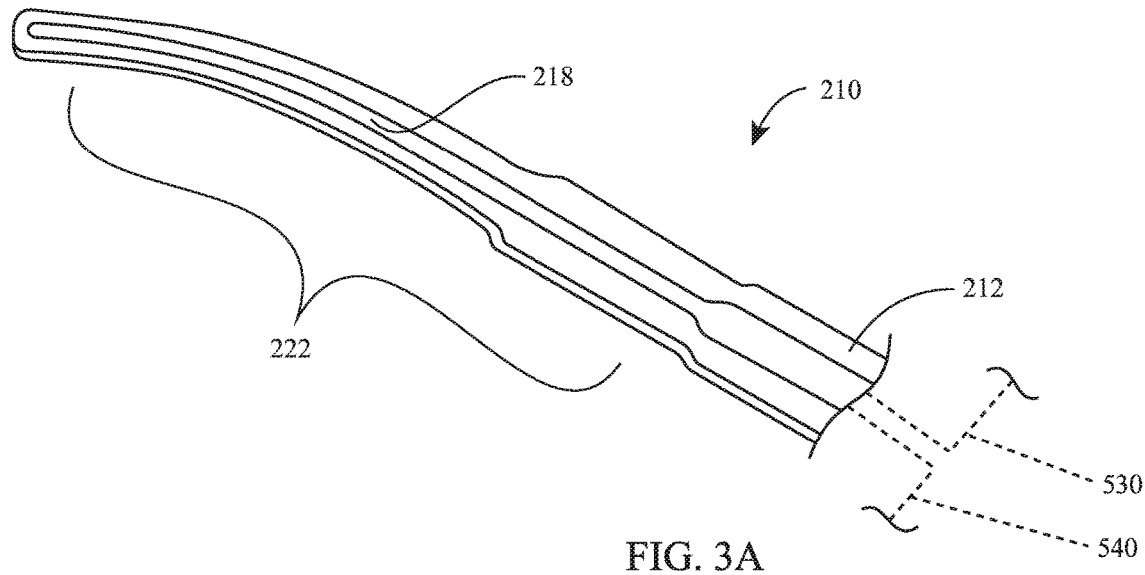
FIG. 3A is a longitudinal, cross-sectional view of a distal end portion of the waveguide of FIG. 2 including a lumen defined therethrough.

Referring also to FIG. 3A, body portion 212 of waveguide 210 and/or blade 222 may be formed to include a longitudinally-extending lumen 218 defined through at least a portion thereof. Lumen 218 may define a constant diameter, varying diameter, or other suitable configuration, and may follow the curvature of blade 222 or define a different curvature, for example. Lumen 218 may define a closed distal end portion that is proximally-spaced from the distal end portion of blade 222, or may include an open distal end portion. Lumen 218 may include an open proximal end portion (not shown) at the proximal end portion of waveguide 210. Alternatively, the open proximal end portion (not shown) of lumen 218 may be defined through a side surface of blade 222 or body portion 212 of waveguide 210 at any suitable position along the length thereof. As detailed below, lumen 218 enables flow and/or circulation of cooling fluid through waveguide 210 and/or blade 222 to cool waveguide 210 and blade 222 before, during, and/or after use.

Figure 3B:
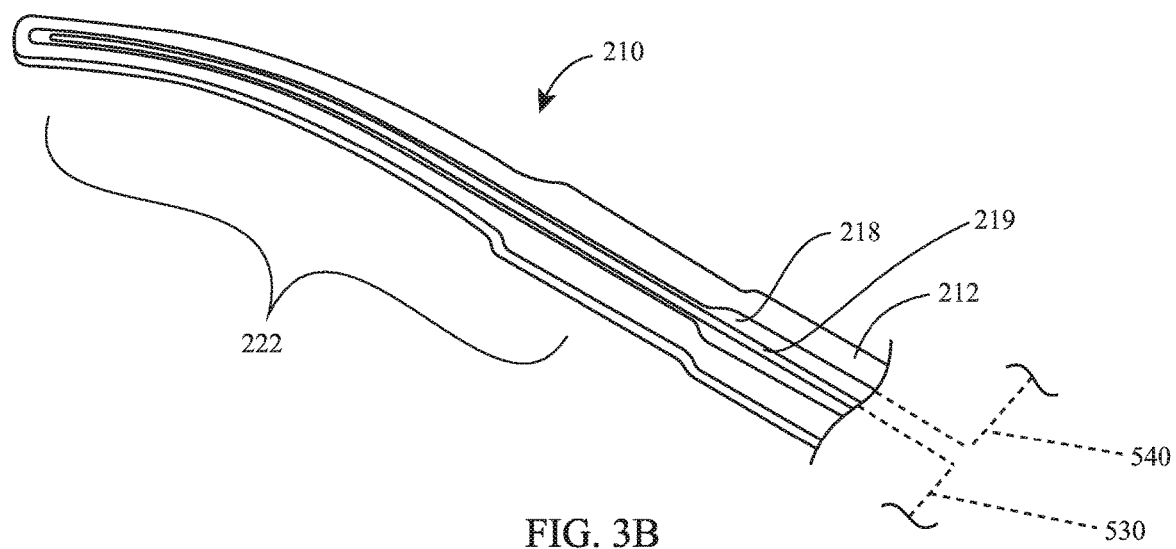
FIG. 3B is a longitudinal, cross-sectional view of the distal end portion of the waveguide of FIG. 2 including an inner tube extending through the lumen.

Referring to FIGS. 2 and 3B, waveguide 210 and/or blade 222 may additionally be formed to include an inner tube 219 extending at least partially through longitudinally-extending lumen 218. Alternatively, inner tube 219 may be inserted into lumen 218 after formation of waveguide 210 and blade 222. In either configuration, inner tube 219 may define a constant diameter, varying diameter, or other suitable configuration. Inner tube 219 may define an open distal end portion and/or may include apertures, slots, etc. (not shown) defined therethrough at one or more locations along a length thereof. As detailed below, inner tube 219 cooperates with lumen 218 to enable circulation of cooling fluid through waveguide 210 and/or blade 222 to cool waveguide 210 and blade 222 before, during, and/or after use.

Referring again to FIG. 1, TAG 300 is configured to convert electrical energy provided by battery assembly 400 into mechanical energy that is transmitted along waveguide 210 to blade 222. More specifically, TAG 300 is configured to convert the electrical energy provided by battery assembly 400 into a high voltage alternating current (AC) waveform that drives the transducer (not shown) of TAG 300. Activation button 120 of handle assembly 100, as noted above, is electrically coupled between battery assembly 400 and TAG 300. Activation button 120 is selectively activatable in a first position and a second position to supply electrical energy from battery assembly 400 to TAG 300 for operating ultrasonic surgical instrument 10 in a low-power mode of operation and a high-power mode of operation, respectively.

TAG 300 and battery assembly 400 are each removable from handle assembly 100 (together or separately) to facilitate disposal of handle assembly 100 after a single use or to enable sterilization of handle assembly 100 for subsequent use. TAG 300 may be configured to withstand sterilization such that TAG 300 may be sterilized for repeated use. Battery assembly 400, on the other hand, is configured to be aseptically transferred and retained within compartment 116 of fixed handle portion 114 of housing 110 of handle assembly 100 such that battery assembly 400 may be repeatedly used without requiring sterilization thereof, although other configurations of TAG 300 and battery assembly 400 are also contemplated.

With reference to FIGS. 1-3B, cooling system 500 includes a cooling module 510, a cooling activation button 520, and inflow and return conduits 530, 540, respectively. Cooling module 510 includes a fluid reservoir 512 and one or more fluid pumps 514 and is disposed within housing 110 of handle assembly 100 or, alternatively, incorporated into TAG 300 or battery assembly 400. Cooling activation button 520 is disposed on housing 110 and operably coupled to cooling module 510 to enable the selective actuation thereof to initiate cooling, although cooling may alternatively or additionally be automatically controlled. Inflow and return conduits 530, 540 are operably coupled between cooling module 510 and lumen 218 (and inner tube 219 (if so provided)) of waveguide 210 and/or blade 222 to supply and retrieve cooling fluid thereto and therefrom, respectively. More specifically, cooling fluid may be pumped from cooling module 510 through inflow conduit 530 into inner tube 219 to exit inner tube 219 near the distal end portion of lumen 218 and may return to cooling module 510 via the annular space of lumen 218 surrounding inner tube 219 and, eventually, return conduit 540. Other configurations are also contemplated.

Referring generally to FIGS. 2-3B, the present disclosure provides methods for manufacturing body portion 212 of waveguide 210, blade 222, or waveguide 210 in its entirety (including body portion 212 and blade 222) to include any or all of the above-noted features, as traditional manufacturing techniques are ineffective at creating such feature or, if possible to create such features, are technically challenging and/or expensive. Such features include, for example and without limitation: a lumen 218 extending the majority (or the entirety) of the length of body portion 212 and into blade 222; a lumen 218 extending through a curved blade 222; a body portion 212 of waveguide 210 and/or blade 222 formed of varying density and/or including a lattice structure; and a body portion 212 of waveguide 210 and/or blade 222 including various different external features.

In order to achieve any or all of the above-noted features, or any other suitable feature, body portion 212 of waveguide 210 and/or blade 222 are manufactured using an additive manufacturing technique (also known as 3D printing). More specifically, body portion 212 of waveguide 210 and/or blade 222 may be manufactured via Direct Metal Laser Sintering (DMLS) or Selective Laser Sintering (SLS). As noted above, body portion 212 of waveguide 210 and/or blade 222 may be manufactured from a metal, e.g., titanium, a titanium alloy, or other suitable metal, or other material. Using an additive manufacturing technique allows the body portion 212 of waveguide 210 and/or blade 222, including the particular features and/or configuration desired, to be modeled using a Computer Aided Design (CAD) program, from which the body portion 212 of waveguide 210 and/or blade 222 is built in layer-by-later fashion via the additive manufacturing technique, e.g., Direct Metal Laser Sintering (DMLS) or Selective Laser Sintering (SLS). Tube 219, if provided, may be formed within lumen 218 of body portion 212 of waveguide 210 and/or blade 222 as part of the additive manufacturing technique or may be inserted into lumen 218 and subsequent to manufacture of body portion 212 of waveguide 210 and/or blade 222.

While several embodiments of the disclosure have been shown in the drawings and described hereinabove, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing an ultrasonic transmission component of an ultrasonic surgical instrument, comprising:
    forming, via additive manufacturing, a waveguide, including:
        a body portion;
        a curved blade extending distally from the body portion,
        wherein the waveguide is formed to define a lumen extending continuously through a portion of the body portion and a portion of the curved blade; and inserting an inner tube into the lumen of the waveguide, the inner tube extending continuously inside the lumen between the body portion and the curved blade.

2. The method according to claim 1, wherein forming the waveguide via additive manufacturing includes forming the waveguide via Direct Metal Laser Sintering.

3. The method according to claim 1, wherein forming the waveguide via additive manufacturing includes forming the waveguide via Selective Laser Sintering.

4. The method according to claim 1, further comprising:
modeling the waveguide using a computer-aided design program,
wherein the modeled waveguide is utilized to form the waveguide via additive manufacturing.

5. The method according to claim 1, wherein the lumen extends a majority of a length of the body portion and a majority of a length of the curved blade.

6. The method according to claim 5, wherein the lumen defines a closed distal end portion.

7. The method according to claim 1, wherein the waveguide is formed from titanium.

8. The method according to claim 1, wherein at least one of the body portion or the curved blade of the waveguide is formed to include a varied density.

9. The method according to claim 1, wherein at least a portion of at least one of the body portion or the curved blade of the waveguide is formed to include a lattice structure.

10. A method of manufacturing an ultrasonic transmission component of an ultrasonic surgical instrument, comprising:
forming, via additive manufacturing, a waveguide, including:
a body portion;
a blade extending distally from the body portion, wherein at least one of the body portion or the blade defines a varied density,
wherein the waveguide is formed to define a lumen extending continuously through a portion of the body portion and a portion of the curved blade; and
inserting an inner tube into the lumen of the waveguide, the inner tube extending continuously inside the lumen between the body portion and the blade.

11. The method according to claim 10, wherein forming the waveguide via additive manufacturing includes forming the waveguide via Direct Metal Laser Sintering.

12. The method according to claim 10, wherein forming the waveguide via additive manufacturing includes forming the waveguide via Selective Laser Sintering.

13. The method according to claim 10, further comprising:
modeling the waveguide using a computer-aided design program,
wherein the modeled waveguide is utilized to form the waveguide via additive manufacturing.

14. The method according to claim 10, wherein the lumen extends a majority of a length of the body portion and a majority of a length of the blade.

15. The method according to claim 10, wherein the waveguide is formed from titanium.

16. The method according to claim 10, wherein at least a portion of at least one of the body portion or the blade of the waveguide is formed to include a lattice structure.

17. The method according to claim 10, wherein the blade is curved.

* * * * *